US00PP09448P

United States Patent [19]

van Andel

[11] Patent Number: Plant 9,448

[45] Date of Patent: Feb. 6, 1996

[54] ALSTROEMERIA VARIETY NAMED 'STATIREN'

[75] Inventor: Jacob van Andel, Aalsmer, Netherlands

[73] Assignee: Van Staaveren B.V., Aalsmeer, Netherlands

[21] Appl. No.: 372,434

[22] Filed: Jan. 11, 1995

[51] Int. Cl.[6] ..... A01H 5/00

[52] U.S. Cl. ..... Plt./87.1

[58] Field of Search ..... Plt./87.1

*Primary Examiner*—James R. Feyrer

*Attorney, Agent, or Firm*—Christie, Parker & Hale

[57] ABSTRACT

A new and distinct Alstroemeria variety producing flowers of good quality and attractive coloration.

1 Drawing Sheet

BACKGROUND OF THE INVENTION

The present invention relates to a new and distinct variety of Alstroemeria originated as a seedling by crossing as seed parent an unreleased, unpatented seedling identified as 86R1684-1 and as pollen parent an unreleased, unpatented seedling identified as 87G1069-21 from among my collection of Alstroemeria seedlings maintained under controlled conditions in a greenhouse at Van Staaveren B.V., Aalsmeer, The Netherlands, for developmental purposes. The varietal denomination of the new variety is 'Statiren'.

The first act of asexual reproduction of 'Statiren' was in Aalsmeer, The Netherlands, by propagation by dividing rootstocks. Asexual reproduction through successive generations has demonstrated that the combination of characteristics as herein disclosed for 'Statiren' are firmly fixed and retained through successive generations of asexual reproduction.

'Statiren' has not been observed under all possible environmental conditions. Phenotypic expression may vary with variations in environment such as temperature, light intensity, day length and growing and cultural conditions.

SUMMARY OF THE INVENTION

Flowers of the new variety of Alstroemeria, 'Statiren' are characterized by two concentric circles of three petals of unusual coloration, as described herein.

The plant blooms profusely in the Spring and Fall, which is a desirable characteristic in a cut flower variety. The flower-bearing stems are of excellent quality. 'Statiren' grows productively under greenhouse conditions and is also reproducible both by division of rhizomes and by tissue culture.

DESCRIPTION OF ILLUSTRATIONS

The new variety of Alstroemeria hybrid is illustrated in the accompanying illustration, which shows typical flower characteristics, with colors being as nearly true as is possible for illustrations of this type.

DETAILED DESCRIPTION OF THE NEW VARIETY

The following is a detailed description of the new cultivar of Alstroemeria hybrid as observed in a greenhouse in Aalsmeer, The Netherlands. Color designations indicated are in accordance with The Royal Horticultural Society Colour Chart by color plate designations.

Botanical classification:

*Family.*—Amaryllidaceae.

*Genus.*—Alstroemeria sp.

*Commercial.*—Alstroemeria hybrid.

Origin: Seedling.

PLANT

Form: Bush.

Shape: Upright.

Height: About 125 to 175 cm.

Internode length: About 1 to 4 cm.

Growth rate: Fast; the length of time (number of days) taken from young plants (i.e. rooted rootstocks, the stage of development in which the varieties are sold) to flowering stage under commercial greenhouse conditions is 80–90 days.

Pinching required: No.

Main stem or cane length: About 150 cm.

Growth: Vigorous.

Strength: Strong.

Foliage:

*Quantity.*—Abundant.

*Number of leaves.*—About 30 to 40.

*Size of leaf.*—Length: About 15 to 20 cm. Width: About 2 to 4 cm.

*Shape of leaf.*—Elliptical.

*Margin type.*—Straight.

*Texture.*—Glossy.

*Color.*—Upper side: Near 137A. Underside: Near 137C.

*Rhizomes.*—Yes. Color: Near 155D. Size: About 10–30 cm.

INFLORESCENCE—FLOWER/FLORET

Blooming habit: Continuous.

Are spent umbels required to be pinched to maintain the claimed plant in a continuous blooming condition? No.

Blooms Profusely.

*Spring.*—Yes.

*Fall.*—Yes.

*Has tendency to give few blooms in fall.*—No.

Size: Very large.

*Diameter.*—About 7 cm.

*Depth.*—About 5 cm.

Stage when described: When first anthers release their pollen.

Borne: Singly in simple panicles.

Shape or form:

*When bloom first opens.*—Cup.

*When bloom matures.*—Cup.

Petalage
*Number of petals.*—6.
*Arrangement.*—2 concentric circles of 3 petals.
*Form.*—Obovate.
*Margin type.*—Minutely crimped; outer petals complete.
*Apex.*—Pointed.
*How long do petals stay on stem?*—About 3 weeks.
*Texture.*—Soft.
*Appearance.*—Velvety.
*Color (summer/fall).*—Outer petal/floret: The lamina of the outer layer of petals is generally near 48C with a white base, near 155D; but contain a darker red central brush stroke near 48A; may or may not contain one marking or spot; reverse sides of these petals have similar color patterns. Inner petal/floret: Base and apex of body near 48C with a central broad white band near 155D; the white band of the lateral inner petals having a central bright yellow spot near 3C, absent on the lower inner petal. The two inner lateral petals have 20–30 spots, color near 185A.
Peduncle or flower stem
*Length.*—About 7 to 10 cm.
*Color.*—Near 137B to 137C.
*Strength.*—Strong.
*Upright.*—Yes.
Discoloration after full bloom? Slightly; the main color of petals, near 48A, turns to near 48B to 48C.
Is bloom affected by wet or hot weather? No.
Persistence (does flower hang on and dry?): No.
Disease resistance: Unknown.
Fragrance: None.
Lasting quality:
*On plant.*—About 4 weeks.
*As cut flower.*—About 17 to 22 days.

BUD

Size:
*Diameter.*—About 1 to 2 cm.
*Depth or length.*—About 2 to 4 cm.
Form or shape: Pear-shaped.
*Long.*—Yes.
*Pointed.*—No.
Rate of opening: Fast.
Color of petals/tepals:
*When petals first divide.*—Near 48A.
*When petals begin to unfurl.*—Near 48A.
Peduncle or flower stem:
*Length.*—About 7 to 12 cm.
*Hairy.*—No.
*Strength or character.*—Erect.
*Color.*—Near 137B to 137C.

REPRODUCTIVE ORGANS

Stamen:
*Number.*—6.
*Arrangement.*—Around the style.
Anthers:
*Size.*—About 8 to 10 mm.
*Color.*—Near 152A.
Filaments:
*Length.*—About 5 cm.
*Color.*—Near 48A.
Pollen:
*Color.*—Near 153A.
Pistils:
*Number.*—1.
Styles:
*Length.*—About 4 to 5 cm.
*Color.*—Near 48A.
Stigmas:
*Color.*—Near 48A.

FRUIT

Fertile: No.
Shape: Round.
Color at maturity: Near 163A.

I claim:

1. A new variety of Alstroemeria plant substantially as herein shown and described.

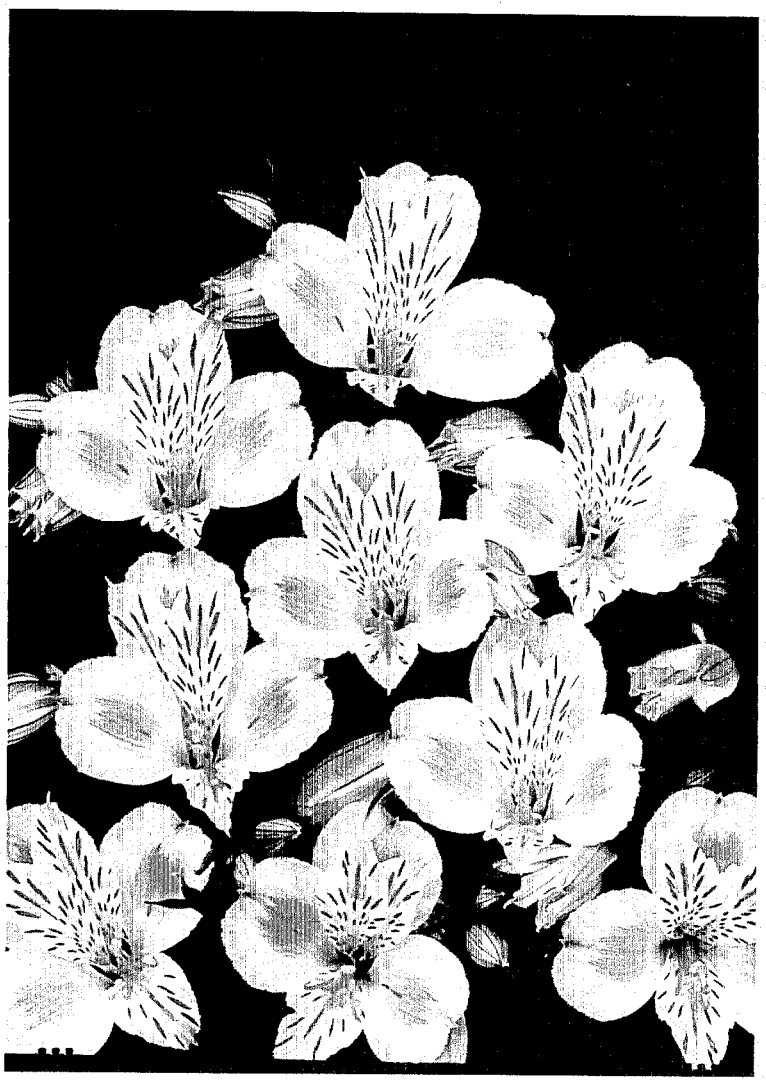

* * * * *